(12) United States Patent
Kimura et al.

(10) Patent No.: US 7,449,577 B2
(45) Date of Patent: Nov. 11, 2008

(54) HIGH PURITY PIPERAZINE PYROPHOSPHATE AND PROCESS OF PRODUCING SAME

(75) Inventors: Ryoji Kimura, Saitama (JP); Hisashi Murase, Saitama (JP); Masaru Nagahama, Saitama (JP); Tetsuo Kamimoto, Saitama (JP); Sinji Nakano, Saitama (JP)

(73) Assignee: Adeka Corporation, Tokyo (JP)

( * ) Notice: Subject to any disclaimer, the term of this patent is extended or adjusted under 35 U.S.C. 154(b) by 325 days.

(21) Appl. No.: 10/563,478

(22) PCT Filed: Aug. 27, 2004

(86) PCT No.: PCT/JP2004/012379

§ 371 (c)(1),
(2), (4) Date: Jan. 5, 2006

(87) PCT Pub. No.: WO2005/037806

PCT Pub. Date: Apr. 28, 2005

(65) Prior Publication Data

US 2006/0167256 A1    Jul. 27, 2006

(30) Foreign Application Priority Data

Oct. 16, 2003 (JP) ............................. 2003-356864

(51) Int. Cl.
*C07F 9/02* (2006.01)

(52) U.S. Cl. .................................................. 544/337

(58) Field of Classification Search ...................... None
See application file for complete search history.

(56) References Cited

U.S. PATENT DOCUMENTS

| 3,810,850 A | 5/1974 | Rowton |
| 4,599,375 A | 7/1986 | Berte' et al. |

FOREIGN PATENT DOCUMENTS

| EP | 126454 | 11/1984 |
| JP | 48-088791 | 11/1973 |
| JP | 2002-371198 | 12/2002 |
| JP | 2003-171548 | 6/2003 |
| JP | 2003-261711 | 9/2003 |

*Primary Examiner*—James O. Wilson
*Assistant Examiner*—Noble Jarrell
(74) *Attorney, Agent, or Firm*—Young & Thompson

(57) ABSTRACT

The present invention provides piperazine pyrophosphate represented by chemical formula (I) which has a sodium content of 10 ppm or lower and a process of producing the same. The piperazine pyrophosphate has high purity and provides a flame retardant composition exhibiting excellent flame retardancy. The process includes dehydration condensation of piperazine diphosphate and is able to produce the piperazine pyrophosphate at low cost.

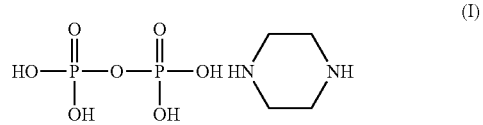

(I)

3 Claims, No Drawings

HIGH PURITY PIPERAZINE PYROPHOSPHATE AND PROCESS OF PRODUCING SAME

TECHNICAL FIELD

This invention relates to piperazine pyrophosphate having a reduced sodium content and a process of producing the same. More particularly, it relates to piperazine pyrophosphate useful as a component of a flame retardant composition added to synthetic resins and to a process of obtaining such piperazine pyrophosphate with high purity at low cost by dehydration condensation of piperazine diphosphate obtained by the reaction between phosphoric acid and piperazine.

BACKGROUND ART

Recently, piperazine pyrophosphate is attracting attention as a component developing an excellent effect in a flame retardant composition added to synthetic resins. A number of reports have been made on the preparation of piperazine pyrophosphate.

For example, Patent Document 1 discloses a process in which piperazine hydrochloride and sodium pyrophosphate are allowed to react in an aqueous solution to give piperazine pyrophosphate as a sparingly water soluble precipitate. Patent Document 2 discloses a process in which anhydrous piperazine and anhydrous sodium pyrophosphate are allowed to react in an aqueous solution, and the reaction system is treated with hydrochloric acid to give piperazine pyrophosphate as a sparingly water soluble precipitate. Patent Document 3 teaches a process in which sodium pyrophosphate is treated with hydrochloric acid, and the resulting pyrophosphoric acid is allowed to react with hydrazine in an aqueous solution to form piperazine pyrophosphate as a sparingly water soluble precipitate.

In the processes disclosed in these references, however, it is difficult in practice to completely remove by-produced sodium chloride or sodium piperazine pyrophosphate by washing with water. It is known that, when piperazine pyrophosphate from a system containing a residual alkaline substance is applied to semiconductor devices, electronic equipment, etc., the alkaline substance generally gives adverse influences. Moreover, production by these processes involves high cost because (1) the production yield is low, (2) the raw materials are expensive, (3) waste disposal is costly, or (4) use of hydrochloric acid necessitates use of a glass-lined reaction vessel.

Patent Document 1: JP-A-48-88791
Patent Document 2: U.S. Pat. No. 3,810,850
Patent Document 3: U.S. Pat. No. 4,599,375

DISCLOSURE OF THE INVENTION

Problems to be Solved by the Invention:

Problems to be solved associated with use of piperazine pyrophosphate obtained by conventional processes as a component of a flame retardant composition consist in that a synthetic resin containing the flame retardant composition exhibits unsatisfactory physical properties by the influences of the impurity, that a flame retardant composition exhibiting excellent flame retardancy was not obtained by the influences of the impurity, and that the conventional processes were unable to produce piperazine pyrophosphate at low cost.

Accordingly, an object of the present invention is to provide high purity piperazine pyrophosphate providing a flame retardant composition exhibiting excellent flame retardancy and a process of preparing such piperazine pyrophosphate at low cost.

Means for Solving the Problems:

The present inventors have conducted extensive investigations to solve the problems and as a result found that use of piperazine pyrophosphate having an impurity content controlled below a specific level provides a flame retardant composition exhibiting excellent flame retardancy and that such piperazine pyrophosphate can be provided by dehydration condensation of piperazine diphosphate. The present invention has been reached based on these findings.

The present invention provides piperazine pyrophosphate represented by chemical formula (I) shown below and having a sodium content of 10 ppm or lower.

[Chemical Formula 1]

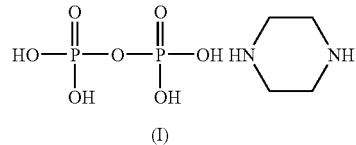

(I)

The present invention also provides a process of producing the piperazine pyrophosphate including dehydration condensation of piperazine diphosphate.

BEST MODE FOR CARRYING OUT THE INVENTION

The piperazine pyrophosphate and the process of producing the same according to the present invention will be described in detail with particular reference to the preferred embodiments thereof.

The piperazine pyrophosphate of the invention has a sodium content of 10 ppm or lower. Having a sodium content of 10 ppm or lower, the piperazine pyrophosphate of the invention provides a flame retardant composition exhibiting excellent flame retardancy without impairing the physical properties of a resin in which the composition is incorporated.

Impurities that can be present in the piperazine pyrophosphate of the invention include sodium chloride, orthophosphoric acid, and triphosphoric acid. The total content of these impurities in the piperazine pyrophosphate of the invention is preferably not more than 5% by weight.

The piperazine pyrophosphate of the invention which is represented by chemical formula (I) and has a sodium content of 10 ppm or less can be obtained through dehydration condensation of piperazine diphosphate. Dehydration condensation of piperazine diphosphate can be carried out by, for example, heating piperazine diphosphate at 120° to 320° C. for 0.5 to 3 hours.

Piperazine diphosphate is obtainable by allowing two equivalents of orthophosphoric acid and one equivalent of piperazine to react in accordance with the reaction scheme in Chemical Formula 2 shown below. The reaction can be performed by heating in a solvent, such as water or methanol, at 200° to 250° C. for 0.5 to 1 hour.

[Chemical Formula 2]

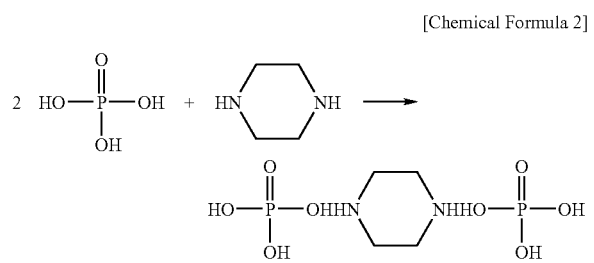

Means for effecting the dehydration condensation reaction of piperazine diphosphate is not particularly limited as long as heating and dehydration may be conducted. Useful means include heating/kneading equipment, hot-air drying equipment, and a dehydration method by refluxing in a solvent.

In the method using heating/kneading equipment, piperazine diphosphate is dehydrated and condensed at a heating temperature of 120° to 320° C., a raw material feed rate of 20 to 100 kg/h, and a number of revolutions of 60 to 1600 rpm. Common equipment for kneading can be employed with no particular restrictions as long as a desired piperazine pyrophosphate product can be produced in large quantities economically. Examples of the equipment include an extruder, a Henschel mixer, a flash mixer, a paddle mixer, a Banbury mixer, a grinding mixer, an SC processor, a Plastomill, a KRC kneader, a vacuum kneader, and a pressure kneader. Among them an extruder and a Henschel mixer are suited because the contact between the contents and the equipment is minimized to help the reaction proceed efficiently.

In the method using hot air drying equipment, piperazine diphosphate is condensed with dehydration at a hot air temperature of 200° to 350° C. Common hot air drying equipment can be employed with no particular restrictions as long as a desired piperazine pyrophosphate product can be produced in large quantities economically. Examples of the equipment include a fluidized bed dryer, a vibrating dryer, a vibrating fluidized bed dryer, a stirring dryer, a flash dryer, a through-flow dryer, a shelf dryer, Dry Mystar, a drum dryer, an air dryer, a microwave dryer, a spray dryer, a disc dryer, a conical dryer, a paddle dryer, a hopper dryer, and a rotary dryer.

The method of dehydration in a refluxing solvent is a method in which piperazine diphosphate is dehydrated and condensed in a high boiling inert solvent at 120° to 320° C. in the presence of 0 to 5% by weight, based on the piperazine diphosphate, of a catalyst.

The high boiling inert solvent is a solvent having a boiling point at or above the boiling point of water and capable of vaporizing together with water. Examples of such solvents include IP2028 and IP1620 (both from Idemitsu Petrochemical Co., Ltd.), normal paraffin, liquid paraffin, xylene, cumene, BTX, 1,2,4-trimethylbenzene, n-undecane, n-dodecane, n-tridecane, n-tetradecane, decaline, dipentene, bicyclohexyl, ethylcyclohexane, p-menthane, camphor oil, turpentine oil, and pine oil. The high boiling inert solvent preferably has a boiling point of 100° to 350° C. Preferred of the examples are IP2028 and liquid paraffin because of their boiling points appropriate for producing high purity piperazine pyrophosphate with good efficiency. The high boiling inert solvent is preferably used in an amount of 50 to 500 parts by weight per 100 parts by weight of piperazine diphosphate.

The catalyst includes boron phosphate, phosphoric acid, zinc oxide, titanium oxide, and aluminum oxide, with boron phosphate and phosphoric acid being preferred for capability of accelerating the reaction. A catalyst is not always necessary.

The piperazine pyrophosphate produced by dehydration condensation of piperazine diphosphate is substantially free from impurities and excellent in physical properties such as heat resistance and water resistance.

Excellent in water resistance, the piperazine pyrophosphate obtained by the process of the present invention is suited for use as a flame retardant for resins. Excellent in heat resistance, it suffers from no change in composition when exposed to molding temperatures as a flame retardant of resins. The piperazine pyrophosphate of the invention can be applied to various resins. The resins include thermoplastic resins and thermosetting resins. The thermoplastic resins include polyolefins and olefin copolymers, such as $\alpha$-olefin polymers, e.g., polypropylene, high-density polyethylene, low-density polyethylene, linear low-density polyethylene, polybutene-1, and poly-3-methylpentene, an ethylene-vinyl acetate copolymer, and an ethylene-propylene copolymer; halogen-containing resins, such as polyvinyl chloride, polyvinylidene chloride, chlorinated polyethylene, chlorinated polypropylene, polyvinylidene fluoride, chlorinated rubber, a vinyl chloride-vinyl acetate copolymer, a vinyl chloride-ethylene copolymer, a vinyl chloride-vinylidene chloride copolymer, a vinyl chloride-vinylidene chloride-vinyl acetate terpolymer, a vinyl chloride-acrylic ester copolymer, a vinyl chloride-maleic ester copolymer, and a vinyl chloride-cyclohexyl maleimide copolymer; petroleum resins, coumarone resins, polystyrene, polyvinyl acetate, acrylic resins; copolymers of styrene and/or $\alpha$-methylstyrene and other monomer(s) (e.g., maleic anhydride, phenylmaleimide, methyl methacrylate, butadiene, and acrylonitrile), such as AS resins, ABS resins, MBS resins, and heat resistant ABS resins; polymethyl methacrylate, polyvinyl alcohol, polyvinyl formal, polyvinyl butyral; linear polyesters, such as polyethylene terephthalate and polybutylene terephthalate; polyphenylene oxide; polyamides, such as polycaprolactam and polyhexamethylene adipamide; polycarbonate, polycarbonate/ABS resin, branched polycarbonate, polyacetal, polyphenylene sulfide, polyurethane, and cellulosic resins; and mixtures of these resins. The thermoplastic resins include phenol resins, urea resins, melamine resins, epoxy resins, and unsaturated polyester resins. Preferred of the recited resins are polypropylene resins.

When the piperazine pyrophosphate of the invention is used as a flame retardant, it is preferably added in an amount of 20 to 60 parts by weight per 100 parts by weight of the resin. The piperazine pyrophosphate of the invention can be used in combination with other flame retardants, such as melamine pyrophosphate, piperazine polyphosphate, melamine polyphosphate, polyphosphoric acid amide, phosphoric esters, and phosphoric ester amides; and compounding additives, such as polysiloxane compounds, metal oxides, silicon dioxide, and higher aliphatic carboxylic acids. The amount of the other flame retardants to be used in combination is preferably 50 to 400 parts by weight per 100 parts by weight of the piperazine pyrophosphate of the invention. The amount of the compounding additives to be used in combination is preferably 0.05 to 20 parts by weight per 100 parts by weight of the resin. The other flame retardant and compounding additive may previously mixed with the piperazine pyrophosphate of the invention to prepare a flame retardant composition, which can be incorporated into the resin.

EXAMPLE

The present invention will now be illustrated in greater detail with reference to Examples, Comparative Examples, and Application Examples. It should be understood that the invention is not construed as being limited thereto, nevertheless.

The purity, sodium content, and decomposition point of piperazine pyrophosphate products obtained in Examples and Comparative Examples were measured as follows.

(1) Measurement of Purity

Purity was determined using an HPLC available from Senshu Scientific Co., Ltd. (pump: SSC-3150; RI detector: ERC-7515A), a column oven CO-965 from JASCO Corp., and Shodex OH pak column SB-802.5 HQ under conditions of a temperature of 40° C., a flow rate of 1.0 ml/min, and a sensitivity of $32 \times 10^{-5}$ RIU/F.S.

(2) Measurement of Sodium Content

The sodium content was determined by elemental analysis with an ICP-AES instrument.

(3) Measurement of Decomposition Point

TG analysis was carried out. The temperature at 5% weight loss (the temperature at which the sample's weight reduced by 5 wt %) was read as a decomposition point.

Example 1

Piperazine diphosphate was kneaded under heat in an extruder (TEX44αII-52.5BW from The Japan Steel Works, Ltd.) under conditions of a cylinder temperature of 230° to 280° C., a raw material feed rate of 25 kg/h, and a screw rotation speed of 60 rpm to give piperazine pyrophosphate as a white powder.

Example 2

Piperazine diphosphate weighing 40 kg was kneaded under heat in a Henschel mixer (FM150J/T from Mitsui Mining Co., Ltd.; capacity: 150 L) under conditions of 190° to 250° C. and 704 to 1000 rpm for 1 hour to give piperazine pyrophosphate as a white powder.

Example 3

Piperazine diphosphate weighing 5 kg and 100 g of 75 wt % phosphoric acid were mixed under heat in a Henschel mixer (FM150J/T from Mitsui Mining Co., Ltd.; capacity: 150 L) under conditions of 170° to 250° C. and 990 to 1590 rpm for 1 hour to give piperazine pyrophosphate as a white powder.

Example 4

In a four-necked flask equipped with a stirrer, a dropping funnel, a thermometer, and a Dean-Stark trap were put 30 g of piperazine diphosphate, 100 g of IP2028, and 0.9 g of 85 wt % phosphoric acid and mixed by heating at 210° to 230° C. for 2 hours to give 27.1 g (yield: 97%) of piperazine pyrophosphate as a white powder.

Example 5

In a four-necked flask equipped with a stirrer, a dropping funnel, a thermometer, and a Dean-Stark trap were put 30 g of piperazine diphosphate, 100 g of IP2028, and 0.9 g of boron phosphate and mixed by heating at 210° to 230° C. for 2 hours to give 27.5 g (yield: 98%) of piperazine pyrophosphate as a white powder.

Example 6

In a four-necked flask equipped with a stirrer, a dropping funnel, a thermometer, and a Dean-Stark trap were put 30 g of piperazine diphosphate and 100 g of IP2028 and mixed by heating at 240° to 250° C. for 2 hours to give 26.2 g (yield: 94%) of piperazine pyrophosphate as a white powder.

Example 7

In a four-necked flask equipped with a stirrer, a dropping funnel, a thermometer, and a Dean-Stark trap were put 300 g of piperazine diphosphate and 1000 g of normal paraffin H (from Nippon Oil Corp.) and mixed by heating at 230° to 250° C. for 0.5 hours to give 271.2 g (yield: 97%) of piperazine pyrophosphate as a white powder.

Example 8

Piperazine diphosphate and melamine phosphate were mixed under heat at a weight ratio of 1:1 in an extruder (TEX44αII-52.5BW from The Japan Steel Works, Ltd.) under conditions of a cylinder temperature of 230° to 270° C., a raw material feed rate of 60 kg/h, and a screw rotation speed of 60 rpm to obtain a 1:1 (by weight) mixture of piperazine pyrophosphate and melamine pyrophosphate as a white powder, which was found to have a sodium content of 0 ppm. The 1% weight loss temperature of the mixture was 300° C.

Comparative Example 1

In 300 g of water was dispersed 0.5 mol of sodium pyrophosphate. The dispersion was cooled to 10° C., and 1 mol of hydrochloric acid was added thereto. To the dispersion was added 0.5 mol of piperazine (purity: 97%) dissolved in 800 g of water at 20° C. or lower, whereupon a white solid precipitated. The reaction system was stirred at 10° C. for 3 hours. The white solid was collected by filtration and washed with water. To the filtrate was added 300 g of methanol, and the thus precipitated white solid was collected by filtration and washed with methanol and water. The combined white solid was dried to give 0.23 mol of piperazine pyrophosphate as a white powder.

The purity, sodium content, and decomposition point of the piperazine pyrophosphate products obtained in Examples 1 to 7 and Comparative Example 1 were measured by the above-described methods. The results of measurements are shown in Table 1.

TABLE 1

|  | Example | | | | | | | Comp. Example 1 |
|---|---|---|---|---|---|---|---|---|
|  | 1 | 2 | 3 | 4 | 5 | 6 | 7 |  |
| Yield (%) | — | — | — | 97 | 98 | 94 | 97 | 46 |
| Purity (%) | 100 | 98.6*1 | 98.4*1 | 97.2*1 | 96.9*2 | 100 | 100 | 100 |
| Na Content (ppm) | 0 | 0 | 0 | 0 | 0 | 0 | 0 | 15 |
| Decomp. Point (° C.) | 324 | 317 | 322 | 318 | 323 | 324 | 324 | 326 |

*1 The impurity was orthophosphoric acid.
*2 The impurity was boron phosphate.

Application Example and Comparative Application Example

A hundred parts by weight of a polypropylene (PP) resin (injection molding grade, available from Mitsui Chemicals, Inc.) was compounded with 0.1 part by weight of calcium stearate (lubricant), 0.1 part by weight of tetrakis[methylene-3-(3,5-di-tert-butyl-4-hydroxyphenyl)propionate]methane (phenol antioxidant), and 0.1 part by weight of bis(2,6-di-tert-butyl-4-methylphenyl)pentaerythritol diphosphite (phosphoric acid antioxidant) to prepare a PP resin composition. A flame retardant composition shown in Table 1 and an additive ($SiO_2$) were mixed into the PP resin composition, and the mixture was extruded at 200° to 230° C. to obtain pellets. The resulting pellets were injection molded at 220° C. to prepare a 1.6 mm thick specimen, which was subjected to the UL 94V test according to the following procedure. The piperazine pyrophosphate as prepared was stored at 50° C. under a load of $0.175\,kg \cdot cm^{-1}$ for one week before use as a flame retardant.

UL Flammability 94V Test:

The specimen of 12.7 mm in width, 127 mm in length, and 1.6 mm in thickness was positioned vertically, and a burner flame was applied to the lower end of the specimen for 10 seconds. After 10 seconds, the flame was removed, and the time required to self-extinguish (burning time) was recorded. As soon as the flame extinguished, the flame was immediately applied for another 10 seconds. Again the burning time was recorded. Ignition of the cotton layer put under the specimen by any drips of flaming particles from the specimen was also observed.

The burning time after each flame application and the ignition of the cotton layer were interpreted into a UL-94 flammability rating. The V-0 rating is the lowest flammability. The V-1 rating is less flame retardancy, and V-2 rating is still less flame retardancy. A specimen that was not interpreted into any of these ratings was rated "NR". Furthermore, the oxygen index was measured using the specimens.

TABLE 2

|  | Application Example | | | | | Comp. Appln. Example | |
|---|---|---|---|---|---|---|---|
|  | 1 | 2 | 3 | 4 | 5 | 1 | 2 |
| PP Resin Composition | 73.0 | 73.0 | 73.0 | 73.0 | 73.0 | 73.0 | 73.0 |
| Flame Retardant Composition: | | | | | | | |
| Melamine Pyrophosphate | 10.0 | 12.0 | 15.0 | 18.0 | 20.0 |  | 10.0 |
| Piperazine Pyrophosphate*3 | 20.0 | 18.0 | 15.0 | 12.0 | 10.0 |  |  |
| Ammonium Polyphosphate |  |  |  |  |  | 30.0 | 20.0 |
| $SiO_2$ | 0.3 | 0.3 | 0.3 | 0.3 | 0.3 | 0.3 | 0.3 |

TABLE 2-continued

|  | Application Example | | | | | Comp. Appln. Example | |
|---|---|---|---|---|---|---|---|
|  | 1 | 2 | 3 | 4 | 5 | 1 | 2 |
| UL-94 V (1.6 mm) | V-0 | V-0 | V-0 | V-0 | V-0 | V-2 | V-2 |
| Oxygen Index | 37.0 | 36.5 | 35.0 | 34.0 | 33.0 | 35.0 | 35.0 |

*3 The piperazine pyrophosphate prepared in Example 1.

As is apparent from Table 1, the piperazine pyrophosphate obtained by the process of the present invention has a lower sodium content and achieves a much higher yield than the product obtained by a conventional process. As can be seen from Table 2, the flame retardant compositions containing the piperazine pyrophosphate having a sodium content of 10 ppm or lower that was prepared by the process of the invention achieve satisfactory results in the UL flammability test and high oxygen indices.

It is apparent from these results that use of high purity piperazine pyrophosphate with a sodium content of 10 ppm or lower provides a flame retardant composition exhibiting excellent flame retardancy and that such high purity piperazine pyrophosphate can be obtained by the process of the present invention.

INDUSTRIAL APPLICABILITY

The present invention provides high purity piperazine pyrophosphate and a process of producing such piperazine pyrophosphate at low cost. Use of the high purity piperazine pyrophosphate provides a flame retardant composition exhibiting excellent flame retardancy.

The invention claimed is:

1. A process of producing a piperazine pyrophosphate, said process comprising dehydration condensation of piperazine diphosphate, wherein said piperazine pyrophosphate is of the formula:

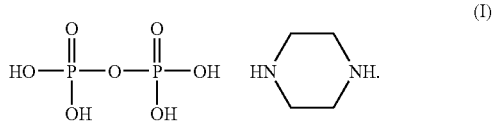

(I)

2. The process of claim 1, wherein the dehydration condensation of piperazine diphosphate is performed using heating/kneading equipment at 120 to 320° C. and a number of revolutions of 60 to 1600 rpm.

3. The process of claim 1, wherein the dehydration condensation of piperazine diphosphate is performed by dehydration in a ref refluxing solvent at 120 to 320° C.

* * * * *